United States Patent
Madonado et al.

(10) Patent No.: US 6,465,795 B1
(45) Date of Patent: Oct. 15, 2002

(54) CHARGE NEUTRALIZATION OF ELECTRON BEAM SYSTEMS

(75) Inventors: Juan R. Madonado, Palo Alto; Lee H. Veneklasen, Castro Valley, both of CA (US); Matthias Brunner, Kirchheim; Ralf Schmid, Poing, both of (DE)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/536,897

(22) Filed: Mar. 28, 2000

(51) Int. Cl.[7] .................. H01J 40/00; H01J 47/00; G01N 23/00; G21R 7/00; G21R 5/10; A61N 5/00; G21G 5/00
(52) U.S. Cl. .................. 250/492.2; 250/492.1; 250/492.22; 250/305; 250/306
(58) Field of Search .................. 250/305, 306, 250/492.1, 492.2, 492.22

(56) References Cited

U.S. PATENT DOCUMENTS

| | | | | |
|---|---|---|---|---|
| 4,859,857 A | * | 8/1989 | Stengl et al. | 250/492.3 |
| 5,164,596 A | * | 11/1992 | Noguchi et al. | 250/309 |
| 5,432,345 A | * | 7/1995 | Kelly | 250/306 |
| 5,563,416 A | * | 10/1996 | Hatakeyama | 250/492.1 |
| 5,625,617 A | * | 4/1997 | Hopkins et al. | 369/121 |

* cited by examiner

Primary Examiner—John R. Lee
Assistant Examiner—David A. Vanore
(74) Attorney, Agent, or Firm—Jung-hua Kuo

(57) ABSTRACT

In a charged particle or electron beam system, gas, such as argon or helium, is introduced over the surface of a substrate and ionized to neutralize charge accumulating on the surface from interactions caused by the impinging charged particles. The gas can be distributed throughout the gas chamber or confined to an area above the substrate. The radiation beam to ionize the gas can be directed across or towards the surface of the substrate. In the latter case, the gas pressure may be reduced to zero.

40 Claims, 3 Drawing Sheets

CHARGE NEUTRALIZATION OF ELECTRON BEAM SYSTEMS

BACKGROUND OF THE INVENTION

1. Field of the Invention

This invention relates to electron beam systems and, more particularly, to neutralizing the charge in such systems.

2. Description of Related Art

Manufacturing semiconductor devices often requires the use of charged particle beams or electron beam (e-beam) systems. The manufacturing process is typically performed using lithographic processes followed by various subtractive (etch) and additive (deposition) processes. Examples of additive processes include deposition of pre-metal dielectric, inter-level dielectric, passivation, and metal layers. Subtractive processes typically involve focusing an electron beam onto the surface of a semiconductor substrate to generate patterns on the substrate. Substrates can include semiconductor wafers, mask plates, printed circuit boards (PCBs), liquid crystal display (LCD) panels, and other various devices. Pattern generation, in which, e.g., CAD patterns are transferred to the surface of the device, can be accomplished using a variety of processes including photolithography, ion beam lithography, and electron beam lithography. In the case of a charged particle system (e.g., e-beam), a precise beam of charged particles is directed to a specific point on the surface of a material, such as photoresist, that is sensitive to relatively small amounts of energy to selectively initiate a response by the material at that point. The beam is selectively directed to various points on the device to create a desired pattern.

An example of a charged particle system is an e-beam system. The e-beam lithography process typically includes first programming a desired image pattern into an e-beam exposure tool. A substrate, such as a silicon wafer, that has been coated with an e-beam sensitive material, such as photoresist, is then mounted within a writing chamber. Once the substrate is secured, the electron beam is selectively brought in contact with the resist, based on the programmed pattern, to create the desired pattern on the resist. The resist can then be processed, e.g., developed and selectively removed, to expose portions of the underlying layer, which can then be etched to form the desired pattern in the substrate.

As seen, in order to accurately transfer the programmed image pattern to the substrate, the pattern must be accurately and precisely reproduced on the photoresist. Various factors can affect the accuracy of the pattern transferred to the resist, including the resolution of the e-beam, the precision of the e-beam tool, the size and density of the features on the pattern, and the placement accuracy of the pattern. The placement accuracy can be adversely affected by charge build-up on the resist. Although, resists are generally non-conductive, the effects of electrons impinging on the resist can cause this charge build-up.

As the electrons in the e-beam or other charged particles impinge and penetrate the photoresist, 1) secondary electrons are emitted and scattered away from the substrate, and 2) the penetrating charged particles undergo an energy loss scattering process, which brings them to rest on the photoresist, where they can remain for several hours after exposure. These two effects result in an accumulation of electrostatic charge and generation of electric fields about these areas. Thus, as the e-beam is scanned or positioned over an adjacent portion of the photoresist to continue defining the desired pattern, the electric field can deflect the e-beam from the path of the programmed pattern and prevent the desired spot on the resist to be selected. The result is a feature that has errors in position and/or size because more or less of the resist is exposed than what was intended. This may occur with either positive or negative polarity resist. For example, with positive resist (in which exposed portions are made more soluble and removed after development), a deflected e-beam may expose more resist than desired, thereby resulting in a longer and/or wider feature. With a negative resist (in which exposed portions are polymerized and unexposed portions are removed), a deflected e-beam may again expose more resist than desired, this time resulting in a shorter and/or narrower feature.

In addition to manufacturing semiconductor devices, electron or charged particle beams are also used to test and analyze or observe such devices. Similar to the above-described effects, the electron beam can be deflected from an intended point or area of the device due to an electric field generated by surface electrons on the device. Also, for example, when analyzing or observing an insulator (non-conducting) material, electrostatic charging can cause errors when measuring secondary electrons emitted from the surface resulting from the impinging e-beam. This can cause measurement inaccuracies, which is particularly important in electron beam testing systems utilized to determine continuity, leakage and open circuits of Liquid Crystal Display (LCD) panels and (PCB) printed circuit boards. In this application, periodic discharging of the panel under test is required. Thus, the charging of the substrate can be the cause of various errors associated with the manufacture and testing of a semiconductor device or other types of devices. These adverse effects become more significant as the devices continue to decrease in size, with critical dimensions decreasing and density increasing.

One method to neutralize this charge accumulation is to deposit a conductive layer on the substrate to remove the surface charge. However, this additional step increases the time and costs for manufacturing the device, as well as possibly introducing defects and increasing the complexity of the device, and it is not easily applicable to the LCD panel or PCB testing.

Accordingly, it is desired to be able to utilize electron or charged particle beams on semiconductor devices and other types of devices without the adverse effects of trapped charge discussed above.

SUMMARY OF THE INVENTION

The present invention introduces a relatively low pressure ionized gas above the surface of a substrate or device to neutralize charge created on the surface by an impinging electron or charged particle beam. Argon, helium, or other suitable gases can be used.

In one embodiment, the gas is introduced throughout the vacuum chamber. A radiation source, such as a vacuum ultraviolet (VUV) radiation lamp or a soft x-ray generator, directs a light or x-ray beam across and above the surface of the substrate. The beam ionizes the gas above the substrate to absorb or neutralize charge accumulated on the surface from the impinging electron beam (e-beam). In some embodiments, the gas is localized or confined to an area over the substrate. In other embodiments, the light or x-ray beam is directed towards the surface of the substrate, either directly by the radiation source or deflected, such as with a perforated mirror. The beam impinging on the substrate creates the photoelectric effect and surface-induced conductivity, which augments the effect of the ionized gases, thereby reducing the neutralization time. For some applications, this embodiment allows the reduction of the gas pressure to zero (no gas) and the utilization of only the photoelectric effect and/or surface induced conductivity to discharge the substrate.

In a particular embodiment of the invention, with a 1 m distance between the electron source and the substrate and utilizing a 10 KeV electron beam, if argon is used, the gas pressure can be up to approximately 1 mTorr, and if helium is used, the pressure can be up to approximately 10 mTorr.

This invention will be more fully understood in light of the following detailed description taken together with the accompanying drawings.

BRIEF DESCRIPTION OF THE DRAWINGS

Use of the same reference symbols in different figures indicates similar or identical items.

DETAILED DESCRIPTION OF THE PREFERRED EMBODIMENTS

According to one aspect of the present invention, a low pressure ionized gas is used to neutralize the surface charge resulting from an electron or charged particle beam impinging on an insulator or semiconductor material. As a result, the charge is neutralized and the electron beam can be scanned across the device without the adverse effects of beam deflection from electrostatic fields due to trapped charge.

Figure 1:
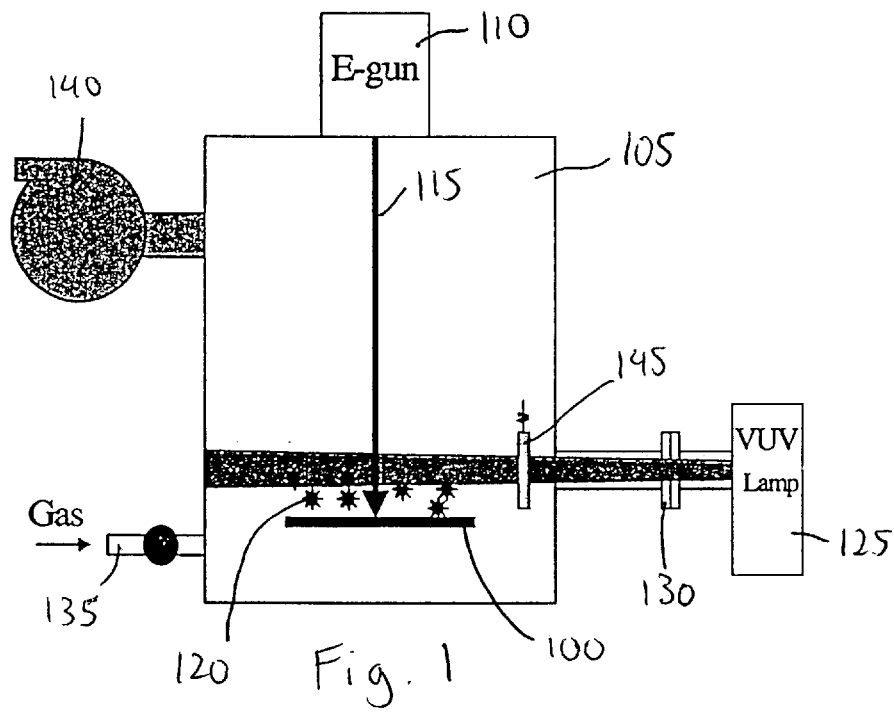
FIG. 1 shows a charged particle system according to one embodiment of the present invention.

FIG. 1 is an illustrative example of a charged particle beam system according to one embodiment of the present invention. A semiconductor substrate 100 is secured within a vacuum chamber 105, which is typically free of air but operating at an elevated pressure of a specific ionizable gas. A charged particle beam generator, such as an electron beam generator 110, is located above substrate 100 to direct a charged particle beam or electron beam (e-beam) 115 onto the surface of substrate 100. E-beam 115 impinges the surface of substrate 100 according to a desired pattern, with e-beam 115 moving across the surface and substrate 100 stationary, substrate 100 moving and e-beam 115 stationary, or both substrate 100 and e-beam 115 moving. Substrate 100 can be any suitable semiconductor device, such as, but not limited to, a silicon wafer, a mask plate, a printed circuit board, or a liquid crystal display panel. The upper surface of substrate 100 is also typically a non-conductive material, such as photoresist or an insulating board. An ionized low pressure gas 120 is allowed to interact with the surface of substrate 100 to neutralize or absorb the charge resulting from e-beam 115 impinging on the surface.

Ionized low pressure gas 120 can be created by ionizing the gas with soft x-rays or vacuum ultraviolet (VUV) radiation. VUV radiation is characterized by wavelengths of less than 200 nm. Soft x-rays, as is known in the art, are characterized by x-rays having comparatively long wavelengths (e.g., 0.5 to 10 nm) and poor penetrating power. The generation of soft x-rays is with known methods, such as by accelerating an electron beam at a predetermined voltage level towards a tungsten target, which, upon contact, generates the soft x-rays. Due to ionization cross sections, soft x-rays are preferred at relatively high pressures. However, electron scattering effects may prevent operation at those pressures, and therefore VUV is preferred for situations where the distance between the electron source and the substrate is relatively large.

According to one embodiment, shown in FIG. 1, VUV radiation is used to generate ionized low pressure gas 120. Light from a VUV lamp 125 is transmitted through a $CaF_2$ or MgF window 130 into vacuum chamber 105, which allows the lamp to be placed at atmospheric pressure outside of vacuum chamber 105 and to be easily replaced. Alternatively, the lamp may be placed inside vacuum chamber 105, thereby eliminating the need for the window 130. The light interacts with a low pressure gas introduced into vacuum chamber 105 via a gas inlet 135. The gas can be any suitable inert gas that does not contaminate the electron source and can be subjected to single or multiple photon ionization from the radiation source, such as argon (Ar) or helium (He). The pressure of the gas is dependent on the type of gas used. The gas pressure is selected to maximize the absorption of the incident radiation from the surface of substrate 100, while minimizing the scattering of electrons in e-beam 115 as they pass through the gas. In general, higher gas pressures generate a greater number of ions, which in turn, increases the absorption of the charge on the substrate surface. Higher gas pressures also reduce the intensity requirements of the electron or charged particle beam source, such as electron beam generator 110. However, higher gas pressures can also degrade the quality of e-beam 115 on its way to substrate 100.

Figure 2:
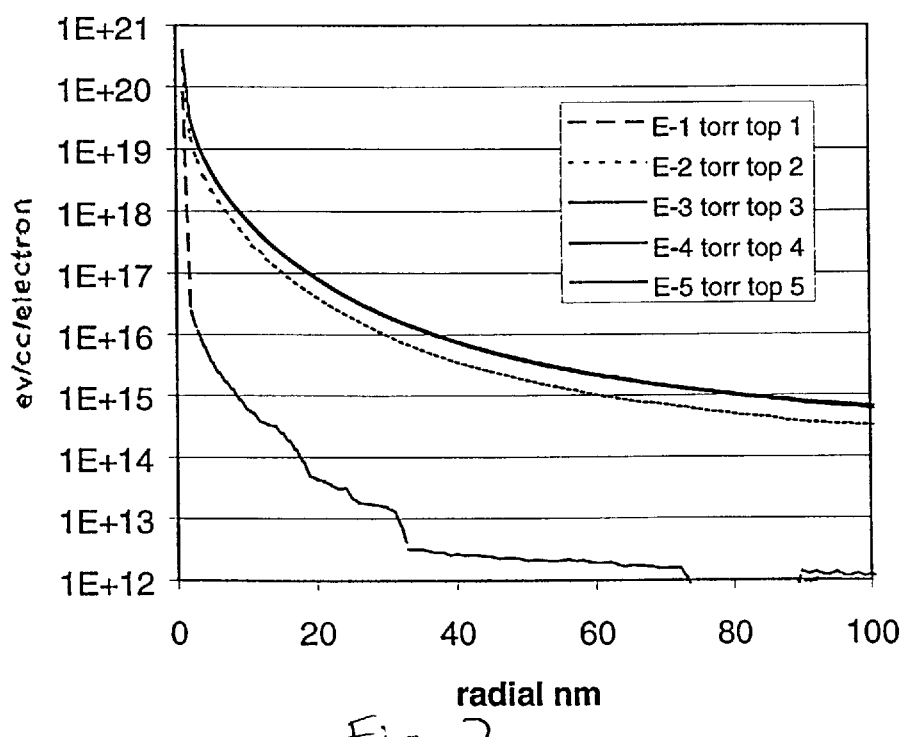
FIG. 2 is a graph showing beam degradation for various gas pressures.

FIG. 2 shows the case of a 10 KeV electron beam exposing a 400 nm thick resist-coated substrate located 1 m away from the source in an argon gas atmosphere. The doses (obtained from the point spread function and Monte Carlo calculations) at the top 100 nm of the resist are plotted as a function of distance from the center of the beam. As seen from FIG. 2, the e-beam is severely affected by argon at 0.1 Torr and is also degraded by argon at 10 mTorr. However, at pressures of 1 mTorr and lower (i.e., the curves for 1 mTorr, 0.1 mTorr, and 0.01 mTorr are approximately the same), there is no appreciable adverse effects on the e-beam. Thus, in this particular embodiment of 10 KeV electrons with a 1 m source-to-substrate distance, if argon is used, the gas pressure could be as high as approximately 1 mTorr. The optimum pressure can be determined experimentally for a given system. Similar simulations have shown that if helium gas is used, there is no significant beam degradation at gas pressures of 10 mTorr or lower. Consequently, when using helium with a 10 KeV electron beam with a 1 m source-to-substrate distance, the gas pressure should be approximately 10 mTorr. Higher pressures can be used when the beam passes through a shorter region of gas.

The electron beam accelerating voltage is determined by the particular system requirements (i.e., lithography, testing, etc). The gas and the UV or soft x-ray radiation are chosen to neutralize the surface charge produced in a given application. The main requirement for the gas is to have a suitably low ionization energy and high cross section to produce the required neutralizing charge from a given photon source without affecting the beam properties that may degrade system performance. The intensity and spectrum of the VUV or soft x-ray radiation is chosen to produce enough ionization in the gas to neutralize the beam induced charge. A pump 140 pumps out gases in vacuum chamber 105 to maintain the desired pressure within chamber 105.

Referring back to FIG. 1, once the desired gas is introduced into vacuum chamber 105 at the appropriate pressure, the gas becomes ionized when it is exposed by the VUV beam. Because the diameter of the VUV beam may not span across the diameter of substrate 100, a rotating (oscillating) mirror 145 can be inserted in vacuum chamber 105 between substrate 100 and window 130. Mirror 145 sweeps the VUV beam across the entire surface of substrate 100, thereby allowing the argon, helium, or other suitable gas to be ionized over the entire surface of substrate 100. Mirror 145 may be made of a material that can reflect the desired radiation. A metal (e.g., Au or Pt) may be utilized. The sweep time may be shorter than the e-beam writing or testing time for a given substrate area to allow uniform illumination during writing and testing.

Thus, according to the present invention, because ionized low pressure gases are generated above the surface of a device or substrate on which an electron or charged particle beam is impinging, any negative charge accumulating on the surface of the substrate is absorbed or neutralized by the ionized gases. Accordingly, the electron or charged particle beam can perform the desired testing or transfer the programmed pattern onto the substrate without being deflected by accumulated charge on the substrate.

Figure 3:
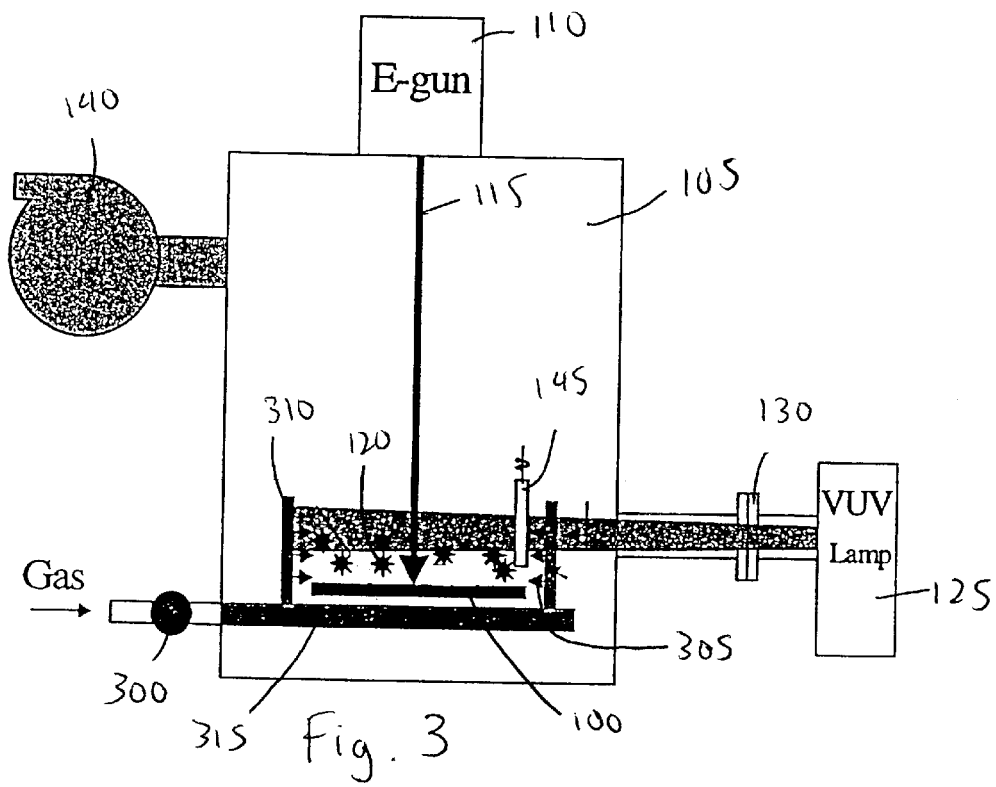
FIGS. 3, 4, and 5 show other embodiments of a charged particle system according to the present invention.
Figure 4:
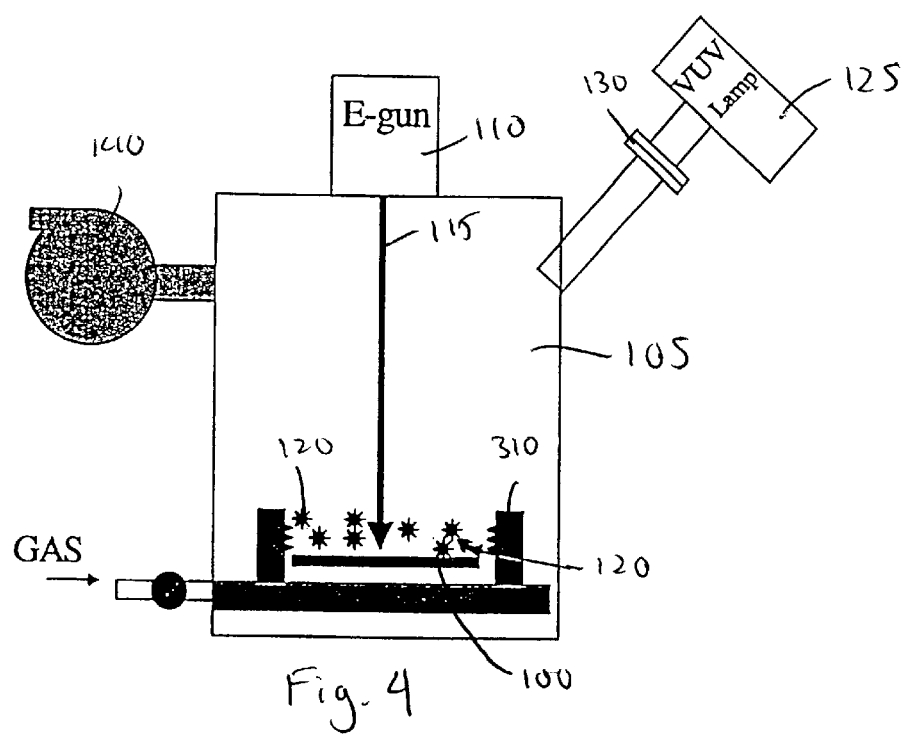
Figure 5:
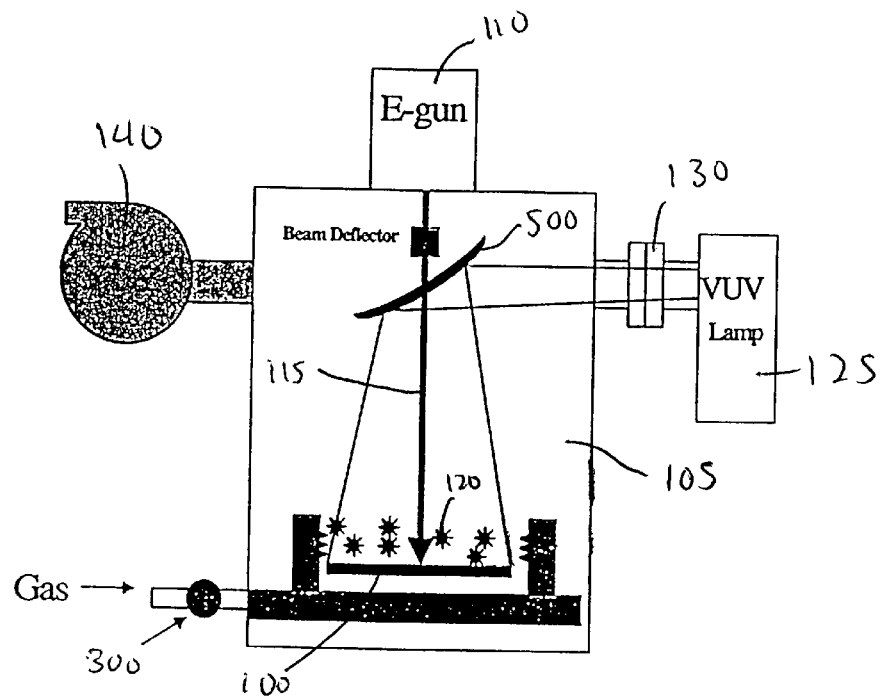

FIGS. 3, 4, and 5 show other embodiments of the invention for ionizing low pressure gas above the surface of a substrate. In FIGS. 3, 4, and 5, instead of the gas being uniformly distributed in vacuum chamber 105 (as shown in FIG. 1), the gas to be ionized is confined to a local area above substrate 100. In this manner, the distance that the electron or charged particle beam has to travel through the gas is decreased, which reduces beam degradation and dispersion. With a higher local pressure, more ions may be generated in the volume near the substrate thereby increasing charge neutralization. Of course, for very high gas pressures, the absorption to the incident radiation increases, and there will be non-uniformities. A relationship between charge neutralization and gas pressure is given in "Neutralization of static electricity by soft X-rays and vacuum UV radiation" by Inaba et al. in Journal of Electrostatics 33 (1994) 15–42, which is incorporated by reference in its entirety.

In FIG. 3, the gas to be ionized is introduced into vacuum chamber 105 via a gas puff valve 300 and gas outlets 305. Gas outlets 305, which direct gas towards substrate 100, are located on the interior of confining walls 310. Gas travels through gas puff valve 300, along a bottom portion 315, and up confining walls 310, where the gas exits into vacuum chamber 105 through gas outlets 305. Confining walls 310 are located at least opposite another. For example, two confining walls 310 can be located across from each other, or two or more pairs of confining walls 310 can be used, with each pair of walls located across from each other, such that substrate 100 is never completely enclosed laterally by confining walls 310. Also, confining walls 310 can completely enclose substrate 100 laterally, with the walls continuous, such as an oval or cylindrical shape, or segmented, such as a polygonal shape. In order to ionize the gas within confining walls 310, the VUV beam must interact with the gas above substrate 100. Thus, at a minimum, the wall between the radiation source, such as VUV lamp 125, and substrate 100 must allow the radiation (e.g., the VUV beam) to pass.

As mentioned above, one advantage of the embodiments shown in FIGS. 3, 4, and 5 is that the gas to be ionized can be maintained a higher pressure within confining walls 310. However, in order to prevent the rest of vacuum chamber 105 from increasing to a pressure that will degrade the quality of e-beam 115, gas puff valve 300 regulates the flow of gas through gas outlets 305. By intermittently introducing the gas when the beam is not being used, rather than continuously, the pressure within vacuum chamber 105 can be maintained at a lower pressure than in the region immediately above substrate 100.

FIGS. 4 and 5 show other embodiments of the present invention, similar to the embodiment shown in FIG. 3, except that the ionizing radiation, e.g., the VUV beam, is directed towards the surface of substrate 100 instead of across the surface. One advantage of this is that the electromagnetic radiation, upon striking the substrate, releases electric charge from the surface in a process known as the photoelectric effect, and it also may induce conductivity on the top illuminated surface of the substrate. Combined with charge neutralization from the ionized gas, this reduces the time required for discharging a negatively charged surface. In some applications, such as those involving a PCB or LCD display, the photoelectric effect alone and the surface induced conductivity may be sufficient to neutralize the charge. Therefore, the gas pressure may be reduced to zero (i.e., no gas in the chamber). For a "thick" PCB or LCD display, no resist is required on the substrate surface, thereby allowing the radiation beam to be broadband. Thick, as defined here, is a thickness of at least approximately 0.3 mm. The intensity of the ionizing radiation can be determined experimentally from the required charge to be neutralized.

In FIG. 4, VUV lamp 125 is positioned so that the VUV beam is directed toward the surface of substrate 100. Even though FIG. 4 shows a diagonal placement, the VUV beam can also be directed into vacuum chamber 105 from above so that the VUV beam is perpendicular to the surface of substrate 100. Regardless of the where the VUV beam enters chamber 105, an oscillating mirror or other suitable device could be located between the radiation source and substrate 100 so that the VUV beam interacts with the gas across the entire surface of substrate 100. In FIG. 5, VUV lamp 125 is positioned above the top of confining walls 305 so that the VUV beam enters vacuum chamber 105 parallel with the surface of substrate 100. A perforated mirror 500, located above substrate 100, redirects and disperses the VUV beam towards the surface of substrate 100. Mirror 500 disperses the VUV beam sufficiently to strike the entire surface of substrate 100 and both ionize the gas and create the photoelectric effect and UV induced conductivity on the substrate surface.

Figure 6:
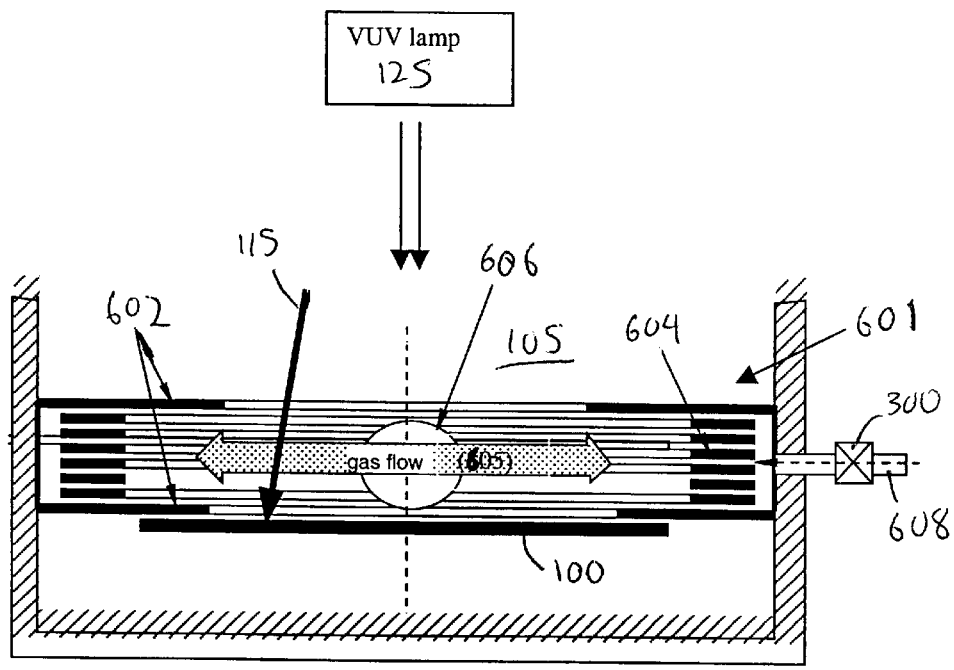
FIG. 6 shows an embodiment to confine gas uniformly to a region near the substrate.

FIG. 6 shows another structure for localizing gas near the substrate. An annular structure 601 surrounds the region just above substrate 100. A plurality of baffles 602 encloses the region of gas flow, with central holes just large enough to allow electron beam 115 to reach the desired field over substrate 100. A stack of annular rings 604 form narrow exit channels that direct gas flow 605 horizontally above substrate 100. More than one gas inlet 608 may be provided to make the pressure more uniform in the inlet manifold within baffles 602. The molecular beam from the gas reservoir outside the rings passes through annular rings 604 toward the surface of substrate 100. A rotating mirror or beam deflector (not shown), similar to that described above with respect to FIGS. 3 and 5, can be used to sweep or disperse the radiation beam across the surface of substrate 100. After passing through this gaseous region above substrate 100, the beam tends to pass through the openings in annular rings 604 instead of dispersing into the rest of vacuum chamber 105, thus reducing the gas load. A differential pumping port 606 into the interior region of baffles 602 is provided. In the case where the hole in the upper one of baffles 602 is small, the gas flow into the upper portion of vacuum chamber 105 is further reduced.

Gas is injected into vacuum chamber 105 through a gas inlet 608 as required to maintain the desired pressure above substrate 100. Similar to the above, puff valve 300 is provided to control gas flow. Gas is introduced into the region inside the stack of annular rings 604. In order to ionize gas above substrate 100, VUV light from VUV lamp 125 is directed above the surface of substrate 100. FIG. 6 shows the VUV light entering from the top of vacuum chamber 105. However, the VUV light can also enter from the sides of vacuum chamber 105, e.g., using several VUV lamps around the chamber with light entering between baffles 602 or using an oscillating mirror, as described above.

The above-described embodiments of the present invention are merely meant to be illustrative and not limiting. It will thus be obvious to those skilled in the art that various changes and modifications may be made without departing from this invention in its broader aspects. For example, the above description shows a single radiation source or VUV lamp. However, more than one radiation source can be used. Further, other methods of dispersing the ionizing radiation across the surface of the substrate can be suitable with the present invention. In addition, the gas pressure may be reduced to zero for the case of the light impinging on the substrate. Therefore, the appended claims encompass all such changes and modifications as fall within the true spirit and scope of this invention.

We claim:

1. A system for neutralizing charge in a charged particle system, comprising:
    a vacuum chamber;
    a substrate located within the vacuum chamber;
    a charged particle source directing a charged particle beam towards the substrate;
    a gas source introducing a gas into the vacuum chamber; and
    a radiation source generating a radiation beam to ionize the gas producing an ionized gas above the substrate, the ionized gas facilitates in neutralizing charge resulting from the charged particle beam.

2. The system of claim 1, wherein the charged particle beam is an electron beam.

3. The system of claim 1, wherein the gas is argon.

4. The system of claim 3, wherein the pressure of the gas is approximately 1 mTorr or less.

5. The system of claim 4, wherein the charged particle beam is an electron beam of approximately 10 keV and the distance from the substrate to the charged particle source is approximately 1 m.

6. The system of claim 1, wherein the gas is helium.

7. The system of claim 6, wherein the pressure of the gas is approximately 10 mTorr or less.

8. The system of claim 7, wherein the charged particle beam is an electron beam of approximately 10 keV and the distance from the substrate to the charged particle source is approximately 1 m.

9. The system of claim 1, wherein the gas is an inert gas.

10. The system of claim 1, wherein the radiation beam is a vacuum ultraviolet radiation beam.

11. The system of claim 1, wherein the radiation beam is a soft x-ray beam.

12. The system of claim 1, wherein the radiation source directs the radiation beam approximately parallel to the surface of the substrate.

13. The system of claim 1, wherein the gas source selectively directs the flow of the gas approximately parallel to and in proximity with the surface of the substrate.

14. The system of claim 13, wherein the gas source comprises an annular structure above the substrate.

15. The system of claim 14, wherein the annular structure comprises a plurality of annular rings spaced closely together to confine the flow of the gas to an approximate planer area above the substrate.

16. The system of claim 13, wherein the gas source comprises a separate enclosed gas inlet chamber and valve.

17. The system of claim 14, wherein the annular structure comprises a plurality of baffles, each of the baffles having at least one central hole allowing the charged particle beam to pass.

18. The system of claim 17, further comprising a differential pump in the region between the plurality of baffles.

19. The system of claim 1, wherein the radiation source directs the radiation beam towards the surface of the substrate.

20. The system of claim 12, further comprising a mirror located within the vacuum chamber and above the substrate to redirect the radiation beam towards the substrate.

21. The system of claim 20, wherein the mirror further disperses the radiation beam across the surface of the substrate.

22. The system of claim 1, wherein the radiation source is located outside the vacuum chamber.

23. The system of claim 22, further comprising a window located between the radiation source and the vacuum chamber, wherein the window is selected from a $CaF_2$ and a $MgF$ window.

24. The system of claim 1, wherein the gas source comprises:
    a valve; and
    vertical walls located within the vacuum chamber and on the outside of the substrate, wherein the vertical walls comprise gas outlets on the interior of the walls.

25. The system of claim 24, wherein the vertical walls are continuous and laterally enclose the substrate.

26. The system of claim 24, wherein the vertical walls comprise at least two vertical walls opposite one another.

27. A method of neutralizing charge in a charged particle system, comprising:
    ionizing a gas above the surface of a substrate located within a charged particle gas chamber to generate an ionized gas, the ionized gas facilitates in neutralizing charge resulting from the charged particle system.

28. The method of claim 27, further comprising directing a charged particle beam towards the surface of the substrate.

29. The method of claim 27, wherein the gas is argon.

30. The method of claim 29, wherein the gas pressure is approximately 1 mTorr or less.

31. The method of claim 30, wherein the charged particle beam is an approximately 10 keV electron beam and the distance from the substrate to a source generating the charged particle beam is approximately 1 m.

32. The method of claim 27, wherein the gas is helium.

33. The method of claim 27, wherein the gas pressure is approximately 10 mTorr or less.

34. The method of claim 33, wherein the charged particle beam is an approximately 10 keV electron beam and the distance from the substrate to a source generating the charged particle beam is approximately 1 m.

35. The method of claim 27, wherein the ionizing comprises:
    introducing the gas into the chamber; and
    directing a radiation beam above the surface of the substrate.

36. The method of claim 35, wherein the radiation beam is directed across the surface of the substrate.

37. The method of claim 35, wherein the radiation beam is directed towards the surface of the substrate.

38. The method of claim 35, wherein the gas is localized above the substrate.

39. The method of claim 38, wherein the gas is introduced intermittently.

40. The method of claim 35, further comprising dispersing the radiation beam towards the substrate.

* * * * *